(12) United States Patent
Pierschbacher et al.

(10) Patent No.: US 7,030,213 B2
(45) Date of Patent: *Apr. 18, 2006

(54) CONFORMATIONALLY STABILIZED CELL ADHESION PEPTIDES

(75) Inventors: Michael D. Pierschbacher, San Diego, CA (US); Erkki I. Ruoslahti, Rancho Santa Fe, CA (US)

(73) Assignee: La Jolla Cancer Research Institute, La Jolla, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/892,071

(22) Filed: Jun. 26, 2001

(65) Prior Publication Data

US 2002/0028913 A1 Mar. 7, 2002

Related U.S. Application Data

(63) Continuation of application No. 09/366,991, filed on Aug. 4, 1999, now Pat. No. 6,353,090, which is a continuation of application No. 08/459,445, filed on Jun. 2, 1995, now Pat. No. 5,981,468, which is a continuation of application No. 08/292,568, filed on Aug. 19, 1994, now Pat. No. 5,906,975, which is a continuation of application No. 08/215,012, filed on Mar. 21, 1994, now abandoned, which is a continuation of application No. 08/124,992, filed on Sep. 21, 1993, now abandoned, which is a continuation of application No. 08/048,576, filed on Apr. 15, 1993, now abandoned, which is a continuation of application No. 07/803,797, filed on Dec. 6, 1991, now abandoned, which is a continuation of application No. 07/292,517, filed on Dec. 29, 1988, now abandoned, which is a continuation-in-part of application No. 07/131,390, filed on Dec. 10, 1987, now abandoned.

(51) Int. Cl.
A61K 38/00 (2006.01)

(52) U.S. Cl. ............ 530/331; 530/317; 514/12; 514/2

(58) Field of Classification Search ......... 530/333, 530/300, 345, 317; 514/12, 9, 2
See application file for complete search history.

(56) References Cited

U.S. PATENT DOCUMENTS

| | | | |
|---|---|---|---|
| 4,517,666 A | 5/1985 | Ando | 369/45 |
| 4,517,686 A | 5/1985 | Ruoslahti et al. | 3/1 |
| 4,547,489 A | 10/1985 | Goldstein | 514/11 |
| 4,578,079 A | 3/1986 | Ruoslahti et al. | 623/11 |
| 4,589,881 A | 5/1986 | Pierschbacher et al. | 623/11 |
| 4,605,512 A | 8/1986 | Schaller et al. | 260/112 |
| 4,614,517 A | 9/1986 | Ruoslahti et al. | 623/11 |
| 4,661,111 A | 4/1987 | Ruoslahti et al. | 623/11 |
| 4,683,291 A | 7/1987 | Zimmerman et al. | 530/324 |
| 4,789,734 A | 12/1988 | Pierschbacher | 530/395 |
| 4,792,525 A | 12/1988 | Ruoslahti et al. | 435/240 |
| 4,857,508 A | 8/1989 | Adams et al. | 514/18 |
| 4,879,313 A | 11/1989 | Tjoeng et al. | 514/616 |
| 4,929,601 A | 5/1990 | Brunetti et al. | 514/18 |
| 4,943,562 A | 7/1990 | Jolles et al. | 514/18 |
| 5,023,233 A | 6/1991 | Nutt et al. | 514/11 |
| 5,037,808 A | 8/1991 | Tjoeng | 514/20 |
| 5,041,380 A | 8/1991 | Ruoslahti et al. | 435/240.2 |
| 5,981,468 A * | 11/1999 | Pierschbacher et al. | |

FOREIGN PATENT DOCUMENTS

| | | |
|---|---|---|
| DE | 3841763 | 6/1990 |
| EP | 0 114 759 | 1/1984 |
| EP | 0 317 053 | 5/1988 |
| EP | 0 275 748 | 7/1988 |
| EP | 0 338 634 | 10/1989 |
| EP | 0 341 915 | 11/1989 |
| EP | 0 368 486 | 5/1990 |
| GB | 2 207 922 | 2/1989 |
| WO | WO 89/00200 | 1/1989 |
| WO | WO 89/04837 | 6/1989 |
| WO | WO 89/05150 | 7/1989 |
| WO | WO 89/07609 | 8/1989 |
| WO | WO 90/00178 | 1/1990 |
| WO | WO 90/02751 | 3/1990 |
| WO | WO 90/06943 | 6/1990 |
| WO | WO 90/15620 | 12/1990 |
| WO | WO 91/01331 | 2/1991 |
| WO | WO 91/15515 | 10/1991 |
| WO | WO 91/15516 | 10/1991 |

OTHER PUBLICATIONS

Hayman et al. 1985 (J. Cell Bio. 100: 1948) (p. 1951, second column, first paragraph).*

Pytela et al., "Platelet membrane glycoprotein IIb/IIIa: member of a family of Arg-Gly-Asp-specific adhesion receptors," Science 231:1559-1562 (1985).

(Continued)

Primary Examiner—Christopher R. Tate
Assistant Examiner—B. Dell Chism
(74) Attorney, Agent, or Firm—McDermott Will & Emery

(57) ABSTRACT

Novel synthetic Arg-Gly-Asp containing peptides which have high affinity and specificity for their receptors by virtue of restrictions on their stereochemical conformation. Such restrictions can be provided by cyclization, by inclusion into a constraining conformational structure such as a helix, by providing an additional chemical structure such as an amide or an enantiomer of a naturally occurring amino acid, or by other methods. In particular, there are provided cyclic peptides having increased affinity and selectivity for the certain receptors over that of linear, Arg-Gly-Asp-containing synthetic peptides.

13 Claims, 4 Drawing Sheets

OTHER PUBLICATIONS

Ratner et al., "Complete nucleotide sequence of the AIDS virus, HTLV-III," *Nature* 313:277-284 (1985).

Rauvala et al., "The adhesive and neurite-promoting molecule p30: analysis of the amino-terminal sequence and production of antipeptide antibodies that detect p30 at the surface of neuroblastoma cells and of brain neurons," *J. Cell. Biol.* 107:2293-2305 (1988).

Recny et al., "Characterization of the α-peptide released upon protease activation of pyruvate oxidase," *J. Biol. Chem.* 260:14287-14291 (1985).

Ruggeri et al., "Inhibition of platelet function with synthetic peptides designed to be high-affinity antagonists of fibrinogen binding to platelets," *Proc. Natl. Acad. Sci. USA* 83:5708-5712 (1986).

Ruoslahti and Pierschbacher, "Arg-Gly-Asp: a versatile cell recognition signal," *Cell* 44:517-513 (1986).

Ruoslahti and Pierschbacher, "Arg-Gly-Asp: a cellular recognition system for positional signal," *Falk. Symposium* 43:239-244 (1987).

Ruoslahti, "Integrins," *J. Clin. Invest.* 87:1-5 (1991).

Sakakibara et al., "Synthesis of (Pro-Hyp-Gly)$_n$ of defined molecular weights evidence for stabilization of collagen triple helix by hydroxypyroline," *BBA* 303:198-202 (1973).

Shebuski et al., "Characterization and Platelet inhibitory activity of bitistatin, a potent Arginine-Glycine-Asparatic acid-containing peptide from the venom of viper *Bitis arietans,*" *J. Biol. Chem.* 264:21550-21556 (1989).

Ali et al., "Potent fibrinogen receptor antagonists bearing conformational constraints," *Peptides Proc. 11th Amer. Peptide Symposium*, La Jolla, CA, Marshall & Rivier, eds. (Jul. 9-14, 1989).

Barker, "Synthesis of cylic hexapeptides containing the Arg-Gly-Asp-Val sequence as potential inhibitors of fibonectin mediated cell adhesion," *Protein Society 2nd Symposium* (1987).

Bodanszky, *Principles of Peptide Synthesis* Springer-Verlag pp. 217-222 (1984).

Bond and Strydom, "Amino acid sequence of bovine angiogenin," *Biochemistry* 28:6110-6113 (1989).

Chao et al., "*Agkistrodon piscivorus piscivirus* platelet aggregation inhibitor: a potent inhibitor of a platelet activation," *Proc. Natl. Acad. Sci. USA* 86:8050-8054 (1989).

Cheresh, "Disialogangliosides GD2 and GD3 are involved in the attachment of human melanoma and neuroblastoma cells to extracellular matrix proteins," *Chem. Abstract* vol. 104, abstract No. 183980c (1986).

D'Souza et al., "Chemical cross-linking of Arginyl-Glycly-Aspartic acid peptides to an adhesion receptor on platelets," *J. Biol. Chem.* 263:3943-3951 (1988).

Davies et al., "Synthetic peptide mimics of the active domain of fibronectin," *Biochem. Soc. Trans.* 18:11326-11328 (1990).

Dayhoff et al., "A model of evolutionary change in proteins," *Atlas of Protein Sequences and Structure* 5:89-99 (1972).

Dennis et al., "Platelet glycoprotein IIb-IIIa protein antagonists from snake venoms: evidence for a family of platelet-aggregation inhibitors," *Proc. Natl. Acad. Sci. USA* 87:2471-2475 (1989).

Drickamer et al., "Mannose-binding proteins isolated from rat liver contain carbohydrate-recognition domains linked to collagenous tails," *J. Biol. Chem.* 261:6878-6887 (1986).

Dufton and Hider, "Conformational properties of the neurotoxins and cytotoxins isolated from elapid snake venoms," *CRC Crit. Rev. Biochem.* 14:113-171 (1983).

Edwards and Spatola, "In vitro activity profiles of cyclic and linear enkephalin pseudopeptide analogs," *Biochem. Biophys. Res. Commun.* 136(2):730-736 (1986).

Gan et al., "A potent platelet aggregation inhibitor from the venom of the viper, *echis carinatus,*" *J. Biol. Chem.* 263 (36):19827-19832 (1988).

Gardner and Hynes, "Interaction of fibronectin with its receptor on platelets," *Cell* 42:439-448 (1985).

Gero and Spatola, "Synthesis and Biological Activity of a cyclic pseudohexapeptide analog of somatostatin," *Biochem. Biophys. Res. Commun.* 120 (3):840-845 (1984).

Garsky et al., "Chemical synthesis of echistatin, a potent inhibitor of platelet aggregation from *Echis carinatus*: synthesis and biological activity of selected analogs," *Proc. Natl. Acad. Sci. USA* 86:4022-4026 (1989).

Gartner and Bennett, "The tetrapeptide analogue of the cell attachement site if fibronectin inhibits platelet aggregation and fibronogen binding to activate platelets," *J. Biol. Chem.* 260:11891-11894 (1985).

Gehlsen et al., "Inhibition of in vitro tumor cell invasion by Arg-Gly-Asp-containing synthetic peptides," *J. of Cell Biology* 106:925-930 (1988).

Ginsberg et al., "Inhibition of fibronectin binding to platelets by proteolytic fragments and synthetic peptides which support fibroblast adhesion," *J. Biol. Chem.* 260:3931-3936 (1985).

Harvey et al., "Toxins from mamba venoms that facilitate neuromuscular transmission" *J. Taxicol.—Toxin Reviews* 3:91-137 (1984).

Haskel and Abendschein, "Deaggregation of human platelets in vitro by an RGD analog antagonist of platelet glycoprotein IIb/IIIa receptors," *Thromb. Res.* 56:687-695 (1988).

Haverstick et al., "Inhibitions of platelet adhesion to fibronectin, fibrinogen and von Willebrand factor substrates by a synthetic tetrapeptide derived from the cell-binding domain of fibronectin, " *Blood* 66:946-952 (1985).

Hruby, "Conformational restrictions of biologically active peptides via amino acid side chain groups," *Life Science*, 31(3):189-199 (1982).

Huang et al., "Tigramin A low molecular weight peptide inhibiting fibrinogen interaction with platelet receptors expressed on glycoprotein IIb-IIIa complex," *J. Biol. Chem.* 262(33):16157-16163 (1987).

Huang et al., "Tigramin: Primary structure and its inhibition of von Willebrand factor binding to glycoprotein IIb/IIIa complex on human platelets," *Biochemistry* 28:661-666 (1989).

Joubert and Taljaard, "Some Properties and the complete primary structures of two reduced and S-Carboxymethylated polypeptides ($S_5C_1$ and $S_5C_{10}$) from *Dendroaspis jamesoni kaimosae* (Jameson's mamba) venom," *Biochem. Biophys. Acta.* 579:228-233 (1979).

Kaiser and Kezdy, "Amphiphilic secondary structure: design of peptide hormones," *Science* 223:249-255 (1984).

Khalil et al., "Affinity of nonhomologous anphiphilic peptides toward a monoclonal antibody raised against apolipoprotein A-I," *Proteins* 1:280-286 (1986).

Kirchofer et al., "Cation-dependent changes in the binding specificity of the platelet receptor GPIIb/IIIa," *J. Biol. Chem.* 265:18525-18530 (1990).

Kieffer and Phillips, Platelet membrane glycoproteins: functions in cellular interactions, *Annu. Rev. Cell Biol.* 36:329-357 (1990).

Kloczewiak et al., "Platelet receptor recognition site on human fibrinogen. Synthesis and structure-function relationship of peptides corresponding to the carboxy-terminal segment of the γ chain," *Biochemistry* 23:1767-1774 (1984).

Lebl et al., "Modification of the disulfide bridge in cyclic melanotropins," *Collection Czechoslavak Chem. Commun.*, 49:2680-2688 (1984).

Lash et al., "Synthetic peptides that mimic the adhesive recognition signal of fibronectin: Differential effects on cell—cell and cell-substratum adhesion in embryonic chick cells," *Dev. Biol.* 123:411-420 (1987).

Maes et al., "The complete amino acid sequence of bovine milk angiogenin," *Fed. Europ. Biochem. Soc.* 241:41-45 (1988).

Marx, "Holding the line against heart disease," *Science* 248:1491-1493 (1990).

Moos et al., "Neural adhesion molecule L1 as a member of the immunoglobulin superfamily with binding domains similar to fibronectin," *Nature* 334:701-703 (1988).

Neurath and Strick, "Confronting the hypervariability of an immunodominant epitope eliciting virus neutralizing antibodies from the envelope glycoprotein of the human immunodeficiency virus type 1 (HIV-1)," *Mol. Immun.* 27:539-549 (1990).

Ohlstein et al., "Tissue type plasminogen activator and streptokinase induce platelet hyperaggrebility in the rabbit," *Thromb. Res.* 46:576-585 (1987).

Ohsaku et al., "Electronic structures of collagen model polymers: $(Gly-Pro)_{n'}$ $(Gly-Hyp)_{n'}$ $(Ala-Pro)_{n'}$ $(Ala-Hyp)_{n'}$ $(Gly-Pro-Gly)_{n'}$ $(Gly-Hyp-Gly)_{n'}$ $(Gly-Pro-Pro)_{n'}$ and $(Gly-Pro-Hyp)_{n'}$," *Int. J. Biol. Macromol.* 6:234-240 (1984).

Olson et al., "Primary structure of α-lytic protease: a bacterial homologue of the pancreatic serine proteases," *Nature* 228:438-442 (1970).

Parise et al., "Synthetic peptides derived from fibrinogen and fibronectin change the conformation of purified platelet glycoprotein IIb-IIIa," *J. Biol. Chem.* 262:12597-12602 (1987).

Pelton et al., Conformationally restricted analogs of somatostatin with high μ-opiate receptor specificity, *Proc. Natl. Acad. Sci. USA* 82:236-239 (1985).

Pelton et al., "Design and synthesis of conformationally constrained somatostin analogues with high potency and specificity for μ opioid receptors," *J. Med. Chem*, 29:2370-2375 (1986).

Pierschbacher and Ruoslahti, "Cell attachment activity of fibronectin can duplicate by small synthetic fragments of the molecule," *Nature* 309:30-33 (1984).

Pierschbacher and Ruoslahti, "Variants of the cell recognition site of fibronectin that retain attachment-promoting activity," *Proc. Natl. Acad. Sci. USA* 81:5985-5988 (1984).

Pierschbacher and Ruoslahti, "Influence of stereochemistry of the sequence Arg-Gly-Asp-Xaa on binding specificity in cell adhesion," *J. Biol. Chem.* 262:17294-17298 (1987).

Plow et al., "Arginyl-Glycyl-Asparatic acid sequences and fibrinogen binding to platelets," *Blood* 70:110-115 (1987).

Plow et al., "The effect of Arg-Gly-Asp-containing peptides on fibrinogen and von Willerbran factor binding to platelets," *Proc. Natl. Acad. Sci. USA* 82:8057-8061 (1985).

Poole et al., "Antibodies and a synthetic peptide that block cell-fibronectin adhesion arrest neural crest cell migration in vivo," *Chem. Abstract* vol. 105, abstract No. 169400c (1986).

Pytela et al., "Identification and Isolation of a 140 kd cell surface glycoprotein with properties expected of a fibronectin receptor," *Cell* 40:191-198 (1985).

Pytela et al., "A 125/115-kDa cell surface receptor specific for vitronectin interacts with the arginine-glycine-asparatic acid adhesion sequence derived from fibronectin," *Proc. Natl. Acad. Sci. USA* 82:5766-5770 (1985).

Siebers and Altendorf, "The $K^+$-translocating Kdp-ATPase from *Escherichia coli,*" *Eur. J. Biochem.* 178:131-140 (1988).

Singer et al., "The fibronectin cell attachment sequence Arg-Gly-Asp-Ser promotes focal contact formation during early fibroblast attachment and spreading," *J. Cell. Biol.* 104:573-584 (1987).

Spatola and Edwards, "Synthesis, Charaterization, and structural properties of linear and cyclic enkephalin pseudopeptide Diastereomers," *Biopolymers* 25:s229-s244 (1986).

Spatola and Darlak, "Amide bond surrogates: pseudopeptides and macrocycles," *Tetrahedron* 44(3):821-833 (1988).

Stanfield et al., "Preparation of $β_9β$-dialkyl analogues of cysteine suitable for peptide," *J. Org. Chem.* 51:5153-5156 (1986).

Toda et al., "Fibronectin receptors of human keratinocytes and their expression during cell culture," *J. Cell. Biol.* 105:3097-3104 (1987).

Yamada and Kennedy, "Peptide inhibitors of fibronectin, laminin, and other adhesion molecules: unique and shared features," *Chem. Abstract 107*, abstract No. 5066p (1987).

* cited by examiner

SEQUENCE LISTING

```
<160> NUMBER OF SEQ ID NOS: 15

<210> SEQ ID NO 1
<211> LENGTH: 10
<212> TYPE: PRT
<213> ORGANISM: Artificial Sequence
<220> FEATURE:
<223> OTHER INFORMATION: sythetic peptide
<221> NAME/KEY: MOD_RES
<222> LOCATION: 2
<223> OTHER INFORMATION: Xaa=Penicillamine (Pen)
<221> NAME/KEY: DISULFID
<222> LOCATION: (2)...(9)

<400> SEQUENCE: 1

Gly Xaa Gly Arg Gly Asp Ser Pro Cys Ala
1               5                   10

<210> SEQ ID NO 2
<211> LENGTH: 11
<212> TYPE: PRT
<213> ORGANISM: Artificial Sequence
<220> FEATURE:
<223> OTHER INFORMATION: sythetic peptide
<221> NAME/KEY: MOD_RES
<222> LOCATION: 2
<223> OTHER INFORMATION: Xaa=Pencillamine(Pen)
<221> NAME/KEY: DISULFID
<222> LOCATION: (2)...(10)

<400> SEQUENCE: 2

Gly Xaa Gly Glu Arg Gly Asp Lys Arg Cys Ala
1               5                   10

<210> SEQ ID NO 3
<211> LENGTH: 8
<212> TYPE: PRT
<213> ORGANISM: Artificial Sequence
<220> FEATURE:
<223> OTHER INFORMATION: sythetic peptide
<221> NAME/KEY: BINDING
<222> LOCATION: (1)...(7)
<223> OTHER INFORMATION: cyclerized by peptide bond

<400> SEQUENCE: 3

Gly Arg Gly Asp Ser Pro Asp Gly
1               5

<210> SEQ ID NO 4
<211> LENGTH: 4
<212> TYPE: PRT
<213> ORGANISM: Artificial Sequence
<220> FEATURE:
<223> OTHER INFORMATION: sythetic peptide
<221> NAME/KEY: MOD_RES
<222> LOCATION: 4
<223> OTHER INFORMATION: Xaa-(D) Ser
```

```
<400> SEQUENCE: 4

Arg Gly Asp Xaa
 1

<210> SEQ ID NO 5
<211> LENGTH: 6
<212> TYPE: PRT
<213> ORGANISM: Artificial Sequence
<220> FEATURE:
<223> OTHER INFORMATION: sythetic peptide

<400> SEQUENCE: 5

Phe Arg Gly Asp Ser Pro
 1               5

<210> SEQ ID NO 6
<211> LENGTH: 6
<212> TYPE: PRT
<213> ORGANISM: Artificial Sequence
<220> FEATURE:
<223> OTHER INFORMATION: sythetic peptide

<400> SEQUENCE: 6

Gly Arg Gly Asp Ser Phe
 1               5

<210> SEQ ID NO 7
<211> LENGTH: 6
<212> TYPE: PRT
<213> ORGANISM: Artificial Sequence
<220> FEATURE:
<223> OTHER INFORMATION: sythetic peptide

<400> SEQUENCE: 7

Phe Arg Gly Asp Ser Phe
 1               5

<210> SEQ ID NO 8
<211> LENGTH: 10
<212> TYPE: PRT
<213> ORGANISM: Artificial Sequence
<220> FEATURE:
<223> OTHER INFORMATION: sythetic peptide
<221> NAME/KEY: MOD_RES
<222> LOCATION: 2
<223> OTHER INFORMATION: Xaa=Penicillamine(Pen)

<400> SEQUENCE: 8

Gly Xaa Gly Arg Gly Asp Ser Pro Cys Ala
 1               5                  10

<210> SEQ ID NO 9
<211> LENGTH: 33
<212> TYPE: PRT
<213> ORGANISM: Artificial Sequence
<220> FEATURE:
<223> OTHER INFORMATION: sythetic peptide
<221> NAME/KEY: MOD_RES
<222> LOCATION: 2,5, 8,11,23,26,29,32
<223> OTHER INFORMATION: Xaa=hydroxyproline(Hyp)

<400> SEQUENCE: 9

Pro Xaa Gly Pro Xaa Gly Pro Xaa Gly Pro Xaa Gly Ala Pro Gly Leu
 1               5                  10                  15

Arg Gly Asp Thr Gly Pro Xaa Gly Pro Xaa Gly Pro Xaa Gly Pro Xaa
                20                  25                  30
```

Gly

<210> SEQ ID NO 10
<211> LENGTH: 18
<212> TYPE: PRT
<213> ORGANISM: Artificial Sequence
<220> FEATURE:
<223> OTHER INFORMATION: sythetic peptide
<221> NAME/KEY: MOD_RES
<222> LOCATION: 1
<223> OTHER INFORMATION: Xaa=Succinyl-alanine;
    (SuccAla)
<221> NAME/KEY: MOD_RES
<222> LOCATION: 5,13,16
<223> OTHER INFORMATION: Aib

<400> SEQUENCE: 10

Xaa Leu Glu Glu Xaa Ala Lys Arg Gly Asp Ser Leu Xaa Gly Lys Xaa
 1               5                  10                  15

Ala Lys

<210> SEQ ID NO 11
<211> LENGTH: 9
<212> TYPE: PRT
<213> ORGANISM: Artificial Sequence
<220> FEATURE:
<223> OTHER INFORMATION: sythetic peptide
<221> NAME/KEY: MOD_RES
<222> LOCATION: 2
<223> OTHER INFORMATION: Xaa=Penicillamine(Pen)

<400> SEQUENCE: 11

Gly Xaa Gly Arg Gly Asp Ser Pro Cys
 1               5

<210> SEQ ID NO 12
<211> LENGTH: 8
<212> TYPE: PRT
<213> ORGANISM: Artificial Sequence
<220> FEATURE:
<223> OTHER INFORMATION: sythetic peptide
<221> NAME/KEY: MOD_RES
<222> LOCATION: 1
<223> OTHER INFORMATION: Xaa=cyclo-(1-7)Gly

<400> SEQUENCE: 12

Xaa Arg Gly Asp Ser Pro Asp Gly
 1               5

<210> SEQ ID NO 13
<211> LENGTH: 11
<212> TYPE: PRT
<213> ORGANISM: Artificial Sequence
<220> FEATURE:
<223> OTHER INFORMATION: sythetic peptide
<221> NAME/KEY: MOD_RES
<222> LOCATION: 2
<223> OTHER INFORMATION: Xaa=pencillamine(Pen)
<221> NAME/KEY: BINDING
<222> LOCATION: (2)...(10)
<223> OTHER INFORMATION: peptide bridge

<400> SEQUENCE: 13

Gly Xaa Gly His Arg Gly Asp Leu Arg Cys Ala
 1               5                  10

<210> SEQ ID NO 14
<211> LENGTH: 8
<212> TYPE: PRT

```
<213> ORGANISM: Artificial Sequence
<220> FEATURE:
<223> OTHER INFORMATION: sythetic peptide
<221> NAME/KEY: BINDING
<222> LOCATION: 1
<223> OTHER INFORMATION: t-butyloxycarbonyl (t-Boc)
<221> NAME/KEY: MOD_RES
<222> LOCATION: 2
<223> OTHER INFORMATION: Xaa=Arg(4-toluenesulphonyl; Tos)
<221> NAME/KEY: MOD_RES
<222> LOCATION: 4
<223> OTHER INFORMATION: Xaa=Asp (O-benzyl ester;OBzl)
<221> NAME/KEY: MOD_RES
<222> LOCATION: 5
<223> OTHER INFORMATION: Xaa=Ser(benzyl; Bzl)
<221> NAME/KEY: MOD_RES
<222> LOCATION: 7
<223> OTHER INFORMATION: Xaa=Asp(t-butyl ester;OtBu)
<221> NAME/KEY: BINDING
<222> LOCATION: (8)...(8)
<223> OTHER INFORMATION: phenylacetamidomethly(PAM)

<400> SEQUENCE: 14

Gly Xaa Gly Xaa Xaa Pro Xaa Gly
 1               5

<210> SEQ ID NO 15
<211> LENGTH: 8
<212> TYPE: PRT
<213> ORGANISM: Artificial Sequence
<220> FEATURE:
<223> OTHER INFORMATION: sythetic peptide
<221> NAME/KEY: BINDING
<222> LOCATION: 1
<223> OTHER INFORMATION: Hydrogen
<221> NAME/KEY: MOD_RES
<222> LOCATION: 2
<223> OTHER INFORMATION: Xaa=Arg (4-toluenesulphonyl; Tos)
<221> NAME/KEY: MOD_RES
<222> LOCATION: 4
<223> OTHER INFORMATION: Xaa=Asp(Benzyl ester;OBzl)
<221> NAME/KEY: MOD_RES
<222> LOCATION: 5
<223> OTHER INFORMATION: Xaa=Ser (benzyl;Bzl)
<221> NAME/KEY: MOD_RES
<222> LOCATION: 7
<223> OTHER INFORMATION: Xaa=Asp (hydroxide; OH)
<221> NAME/KEY: BINDING
<222> LOCATION: (8)...(8)
<223> OTHER INFORMATION: Phenylacetamidomethyl; (PAM)

<400> SEQUENCE: 15

Gly Xaa Gly Xaa Xaa Pro Xaa Gly
 1               5
```

CONFORMATIONALLY STABILIZED CELL ADHESION PEPTIDES

This application is a continuation-in-part of U.S. patent application Ser. No. 09/366,991, filed Aug. 4, 1999, issued as U.S. Pat. No. 6,353,0090 on Mar. 5, 2002; which is a continuation of U.S. patent application Ser. No. 08/459,455, filed Jun. 2, 1995, issued as U.S. Pat. No. 5,981,468, on Nov. 9, 1999; which is a continuation of U.S. patent application Ser. No. 08/292,568, filed Aug. 19, 1994, issued as U.S. Pat. No. 5,906,975, on May 25, 1999; which is a continuation of U.S. patent application Ser. No. 08/215,012, filed Mar. 21, 1994, now abandoned; which is a continuation of U.S. patent application Ser. No. 08/124,992, filed Sep. 21, 1993, now abandoned; which is a continuation of U.S. patent application Ser. No. 08/048,576, filed Apr. 15, 1993, now abandoned; which is a continuation of U.S. patent application Ser. No. 07/803,797, filed Dec. 6, 1991, now abandoned; which is a continuation of U.S. patent applciation Ser. No. 07/292,517, filed Dec. 29,1988, now abandoned; which is a continuation-in-part of U.S. patent application Ser. No. 07/131,390, filed Dec. 10, 1987, now abandoned; the entire contents of each of which are incorporated herein by reference.

FIELD OF THE INVENTION

This invention relates generally to peptides and more specifically to peptides which are involved in cell adhesion systems.

BACKGROUND OF THE INVENTION

The adhesion of cells to other cells or to extracellular materials is important to the orderly development and functioning of cells in an organism. Cell adhesion is mediated by certain adhesive legands and corresponding receptors. Among such adhesive ligands are the glyco-proteins fibronectin, vitronectin and collagen. All three contain the tripeptide sequence arginine-glycine-aspartic acid (Arg-Gly-Asp or R-G-D) which appears to function as the primary recognition site for receptors on the surface of cells binding to these molecules. When presented to cells as a peptide-covered surface, synthetic peptides containing the Arg-Gly-Asp sequence promote cell attachment in a manner similar to that of natural fibronectin or vitronectin. In solution, such peptides can inhibit cell attachment to a surface coated with fibronectin, vitronectin, collagen, the peptides themselves or some other adhesive protein having an Arg-Gly-Asp cell attachment site.

Several receptors have now been identified which recognize the Arg-Gly-Asp sequence of their respective ligands. While some of these receptors have affinity for only their specific ligand, others will interact to varying degrees with two or more ligands containing the tripeptide. It therefore appears that while the Arg-Gly-Asp sequence is sufficient for receptor recognition and binding, the remaining amino acid sequence of the peptide may nonetheless be important to the specificity of the ligand-receptor interaction. The precise manner in which the remaining sequence affects binding has, thus far, remained elusive.

One view that has been held by some investigators in the field is that the specificity of a given adhesive protein for its receptor may depend on the presence in the adhesive protein of one or more receptor binding sites other than their Arg-Gly-Asp site. According to this view, the Arg-Gly-Asp site would be a shared binding site and the additional site or sites would be responsible for the specificity (See, for example, Yamada et al., (1987) Biochem. and Biophys. Res. Comm. 144:35; Wright et al., (1987) PNAS 84:1965). An alternative possibility is that the Arg-Gly-Asp sequence provides essentially all of the information for the receptor binding and that it is the conformation of this sequence that gives an adhesion protein its receptor specificity. The binding sites of various peptide hormones are known to be small (Rose et al., (1985) Adv. in Chemistry 37:1) but these peptides generally comprise only about 10 amino acids in total. In contrast, each of the two fibronectin polypeptide chains comprises over 2000 amino acids. The idea that the conformation of a single amino acid triplet could be important to the function of a number of different proteins carrying it is novel.

Synthetic peptides containing the Arg-Gly-Asp sequence are useful in that they can both promote and inhibit cell attachment. There are at least ten different adhesion receptors that are known or suspected to recognize an Arg-Gly-Asp sequence in one or more of the various adhesive proteins. Peptides that reproduce with reasonable accuracy the function of such adhesive proteins or specifically inhibit that function offer a tremendous potential for the manipulation of important physiological events such as thrombosis, metastasis, inflammation, wound healing, and rejection of prosthetic implants.

There thus exists a need for peptides having an amino acid structure that provides the optimum specificity for the receptor of interest. The present invention satisfies this need and provides related advantages as well.

SUMMARY OF THE INVENTION

The present invention involves novel synthetic peptides which have high affinity and specificity for their receptors by virtue of restrictions on their stereochemical conformation. Such restrictions, or stabilizations, can be provided, for example, by cyclization, by inclusion into a constraining conformational structure such as a helix, by providing an additional chemical structure such as an amide or an enantiomer of a naturally occurring amino acids, or by other methods. Such peptides can have a range of numbers of residues, but preferably between 3 and 100, more preferably 7 to 30. In particular, there is provided a cyclic peptide having increased affinity and selectivity for the vitronectin receptor over that of linear, Arg-Gly-Asp-containing synthetic peptides. The affinity and selectivity of the cyclic peptide approaches that of natural vitronectin.

In one aspect, the invention comprises a peptide having about 10 amino acids in which a bridge is formed between amino acids surrounding the Arg-Gly-Asp sequence. A suitable structure is

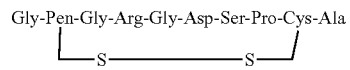

The peptide may have about 1 to 4 amino acids between the Arg-Gly-Asp sequence and those residues forming the bridge. The bridging residues may be, for example, penicillamine and cysteine, or other amino acids capable of forming a bridge, such as a disulfide bridge.

Another suitable structure is

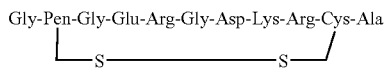

Alternatively, the peptide may be cyclerized through a peptide bond between amino acid residues. An appropriate structure is

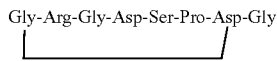

The present invention provides evidence that, rather than the specificity of adhesion ligands residing in distinct binding sites outside the Arg-Gly-Asp site, such specificity results from the conformational structure imposed on the Arg-Gly-Asp sequence by the structure of the remaining peptide. At the practical level, the invention demonstrates that a conformationally restricted Arg-Gly-Asp-containing peptide can have different receptor specificity and higher binding affinity than its unrestricted counterpart. This demonstration permits the synthesis of other Arg-Gly-Asp conformations with variant receptor specificities and affinities.

The stabilized peptides of the present invention have various applications relating to their cell-adhesion properties. In one embodiment, for example, where the peptide structure is

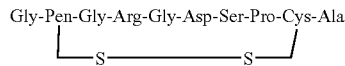

the peptide has increased affinity for the vitronectin receptor and decreased affinity for the fibronectin receptor over that of linear synthetic Arg-Gly-Asp-containing peptides and may therefore be effectively used to inhibit the binding of vitronectin receptor-containing cells to a substrate for cell culture. Alternatively, the stabilized peptide may be usefully employed to promote adhesion of cells expressing the vitronectin receptor by, for example, coating cell culture substrates. Additionally, the stabilized peptide may be used to coat materials for in vitro implantation, such as prothesis, where cell attachment is desired.

BRIEF DESCRIPTION OF THE DRAWINGS

The present invention will be described in connection with the accompanying drawings in which.

DETAILED DESCRIPTION OF THE INVENTION

Figure 1:
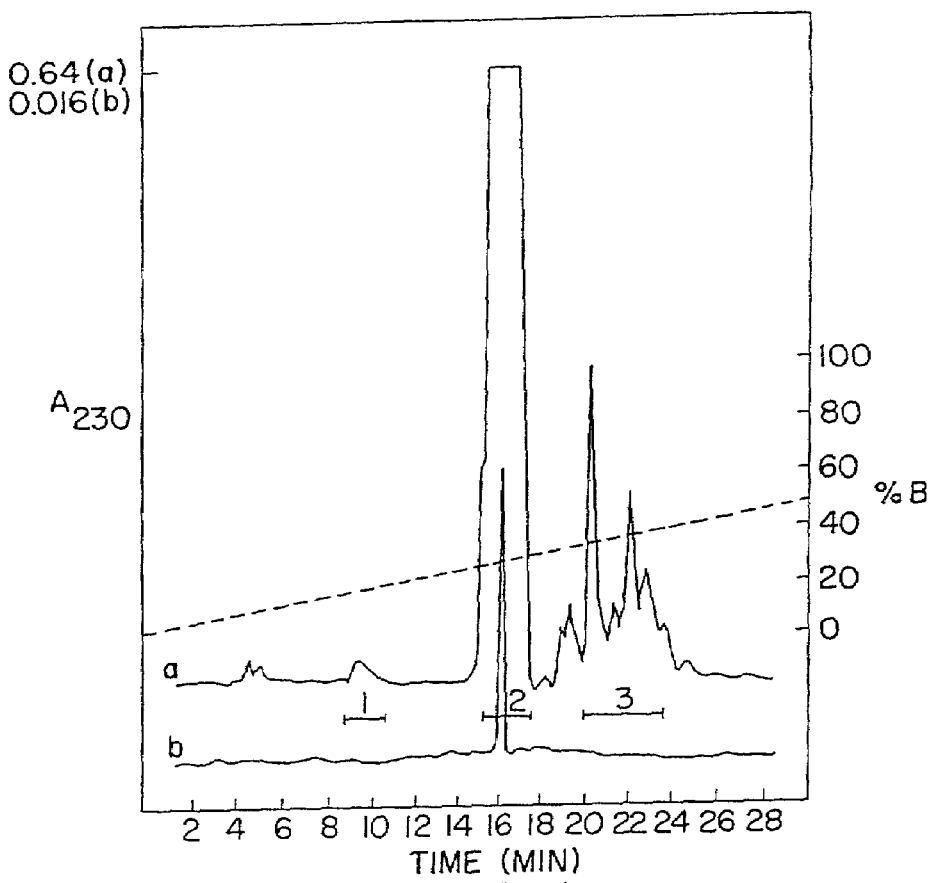
FIG. 1 is a graph of HPLC analysis of a crude preparation of cyclic peptide (a); and purified cyclic peptide (b).

As used herein, the term "conformationally stabilized" or "conformationally constrained" refers to limitations imposed on the number of possible stereochemical structures which a peptide may assume. In the context of the present invention, such limitations are imposed on the conformation of the Arg-Gly-Asp binding site and result from the presence of chemical structures surrounding the binding site which limit the possible structural conformations of the binding site to less than those assumable by the tripeptide sequence alone. Such conformationally stabilized Arg-Gly-Asp-containing peptides still exhibit binding activity with at least one receptor. "Surrounding chemical structures" may refer either to amino acids or other chemical moieties, and may refer both to those moieties lying immediately adjacent the binding site as well as those separated from the binding site itself by the presence of intervening amino acids. The term "amino acids surrounding the Arg-Gly-Asp sequence" refers both to residues adjacent to the Arg-Gly-Asp sequence as well as to residues separated from the Arg-Gly-Asp sequence by intervening residues.

As used herein, references to "Arg-Gly-Asp containing peptides" are intended to refer to peptides having one or more Arg-Gly-Asp containing binding sites which may function as binding sites for a receptor of the "Arg-Gly-Asp family of receptors", i.e., those recognizing and binding to the Arg-Gly-Asp sequence. While the Arg-Gly-Asp sequence has been found to necessarily be invariant in order to retain the binding activity, the composition of the remaining peptide as well as any other chemical moiety present in conjunction with the peptide may vary without necessarily affecting the activity of the binding site. Where specific chemical structures or sequences beyond the Arg-Gly-Asp sequence are presented, it is intended that various modifications which do not destroy the function of the binding site are to be encompassed without departing from the definition of the peptide.

As used herein, the term "bridge" refers to a chemical bond between two amino acids in a peptide other than the amide bond by which the backbone of the peptide is formed.

As used herein, the term "peptide bond" or "peptide linkage" refers to an amide linkage between a carboxyl group of one amino acid and the α-amino group of another amino acid.

The abbreviations for amino acids are used herein are given in the following table:

| Ala | Alanine |
|---|---|
| α-ABA | α-Amino isobutyric acid |
| Arg | Arginine |
| Asp | Aspartic acid |
| Cys | Cysteine |
| Glu | Glutamic acid |
| Gly | Glycine |
| Leu | Leucine |
| Lys | Lysine |
| Pen | Penicillamine |
| Pro | Proline |

| | |
|---|---|
| Ser | Serine |
| SuccAla | Succinyl-alanine |

The present invention provides novel synthetic peptides which incorporate the sequence Arg-Gly-Asp in a conformationally stabilized form. In one embodiment, the peptide comprises the sequence X-$R_1$-$R_2$-Arg-Gly-Asp-$R_3$-$R_4$-Y in which $R_1$ and $R_4$ are amino acids forming or capable of forming a bridge, such as a disulfide bridge, or a peptide linkage, $R_2$ and $R_3$ are each a sequence of 0 to 5 amino acids, X is one or more amino acids or H and Y is one or more amino acids or OH or $NH_2$ and together X and Y preferably total about zero to 100 amino acids, although longer sequences may also be useful. In a preferred embodiment, $R_1$ is penicillamine, $R_4$ is cysteine, $R_2$ is glycine and $R_3$ is Ser-Pro. Additional amino acids can be present at the $NH_2$ and COOH termini, as represented by X and Y, respectively.

Such peptides may be synthesized by any suitable method, including well-known methods of chemical synthesis. Preferably, the linear sequence is synthesized using commercially available automated peptide synthesizers. The material so synthesized can be precipitated and further purified, for example by high performance liquid chromatography (HPLC). Although a purity of greater than 95 percent for the synthesized peptide is preferred, lower purity may be acceptable.

To obtain one of the stabilized peptides of the present invention which has high specificity and affinity for particular cell surface receptors related to the cell adhesion system, the synthesized peptide is cyclized using methods well known in the art. For example, where the residues contain a sulfhydryls, a disulfide bridge may be formed by oxidizing a dilute aqueous solution of the peptide with $K_3[F_e(CN)_6]$. Other means of cyclizing which are known in the art may also be utilized.

The stabilized cyclized peptides of the present invention can also be prepared by forming a peptide bond between non-adjacent amino acid residues. A procedure for forming such peptide bond is provided in Schiller et al., Int. J. Peptide Protein Res. 25:171(1985), which is incorporated herein by reference. Briefly, cyclic peptides can be synthesized on the Merrifield resin by assembling the peptide chain using $N^\alpha$-Fmoc-amino acids and Boc and tertiary-butyl protein.

The stabilized peptide can also be prepared by designing or treating it so as to form a helix such as an alpha ($\alpha$) helix or a triple helix, according to methods well-known in the art.

The stabilized peptides described herein can be used as analogues to adhesion proteins including, for example, vitronectin. Because of the increased affinity for the vitronectin receptor of the cyclic peptide of the preferred sequence over that of the analogous linear sequence, the cyclic peptide may be used to inhibit binding of vitronectin without affecting the function of other receptors such as the fibronectin receptor. Alternatively, the cyclic peptide can be used to promote adhesion of cells expressing the vitronectin receptor, as by coating cell culture substrates.

Certain specific structures containing an Arg-Gly-Asp sequence have been found to confer particular specificity or other attribute on the binding site. Among such structures are the sequences -Arg-Gly-Asp-$NH_2$, -D-Arg-Gly-Asp- and -Arg-Gly-Asp-D-Ser-. The conformationally stabilized latter sequence exhibits useful affinity for the fibronectin receptor but not the vitronectin receptor. The presence of the enantiomeric forms of the naturally occurring amino acids has been shown to confer resistance to degradation enzymes, such as trypsin, in the case of D-Arg. Other useful peptides include the sequences Phe-Arg-Gly-Asp-Ser-Pro, Gly-Arg-Gly-Asp-Ser-Phe, and Phe-Arg-Gly-Asp-Ser-Phe.

The peptides of the present invention may be utilized industrially for in vivo uses such as coating of medical devices, including prostheses or implants, for example vascular implants, so as to facilitate the attachment of cells thereto. In addition, the peptides have in vitro uses in coating of substrates, such as cell culture substrates, to promote cell adhesion.

Other features and advantages of the present invention will become apparent from the following more detailed Examples which illustrate, by way of example, the principles of the invention.

EXAMPLE I

Peptide Synthesis

The peptide Gly-Pen-Gly-Arg-Gly-Asp-Ser-Pro-Cys-Ala was synthesized using an automated peptide synthesizer (Model 430A; Applied Biosystems, Foster City, Calif.) according to the directions provided by the manufacturer. After cleavage from the resin with hydrogen fluoride, the peptides were washed in cold ethyl ether and precipitated from solution in trifluoroacetate with ice cold ether. The peptides were then redissolved in distilled water and lyophilized. The peptides were further purified by HPLC. using a Waters Bondapak™ $C_{18}$ (3×30 cm; 10 μm packing, Waters Assoc., Milford, Mass.).

EXAMPLE II

Cyclization of the Peptide 611 mg of the peptide synthesized as described in Example I were dissolved in 4 liters of water that had been previously boiled and allowed to cool. Immediately prior to addition of the peptide, nitrogen was bubbled through the water for 45 minutes. After the peptide was dissolved, a solution of 0.1 μg/ml of potassium ferrous cyanide $K_3[Fe(CN)_6]$ in water was added dropwise to the stirred peptide solution until the yellow color persisted for 5 minutes (approximately 5 ml). The pH of the solution was held at 7.0 throughout this procedure by addition of $NH_4OH$. The solution was allowed to stand for 20 hours under low vacuum and then lyophilized. Excess $K_3[Fe(CN)_6]$ was removed by passing the cyclized material over a Sephadex G-15 column (1.8×120 cm). The peptide was purified by reverse phase HPLC using a Waters Bondapak™ $C_{18}$ column (3×30 cm; 10 μm packing) (Waters Assoc., Milford, Mass.). The peptide was loaded on the columnm in buffer A (20 mM ammonium acetate at pH 7.5) and eluted with a gradient of buffer B consisting of 60% acetonitrile and 40% buffer A. FIG. 1 depicts the result of purification of the cyclized peptide by reverse phase HPLC. Trace a represents purification of the peptide on the $C_{18}$ column. Fractions 1, 2 and 3 were pooled for testing of their ability to inhibit attachment of cells to fibronectin or vitronectin. Fraction 2, containing cyclic peptide, was rechromatographed by the same procedure on a $C_{18}$ column and yielded a single peak (trace b).

The major peak obtained from the $C_{18}$ column (fraction 2 in FIG. 1) constituted 90% of recovered peptide and was deduced to be a monomeric cyclic peptide because it was retained on the column for the length of time predicted for that sequence and because the uncyclized material and multimeric forms were well separated from the main peak.

EXAMPLE III

Formation of a Triple Helical Structure

Figure 3:
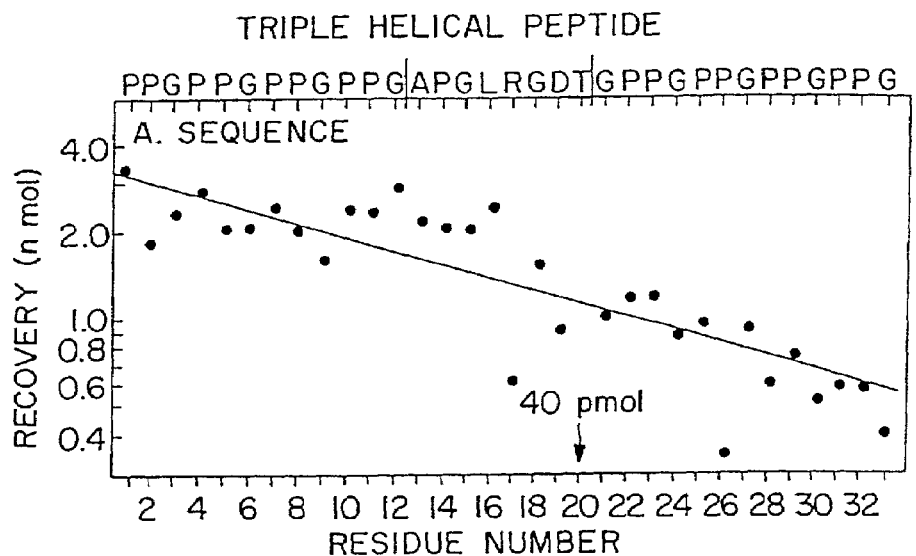
FIG. 3 shows the sequence of the peptide of Example III and the recovery of its degradation products recovered by automated Edman degradation.
Figure 4:
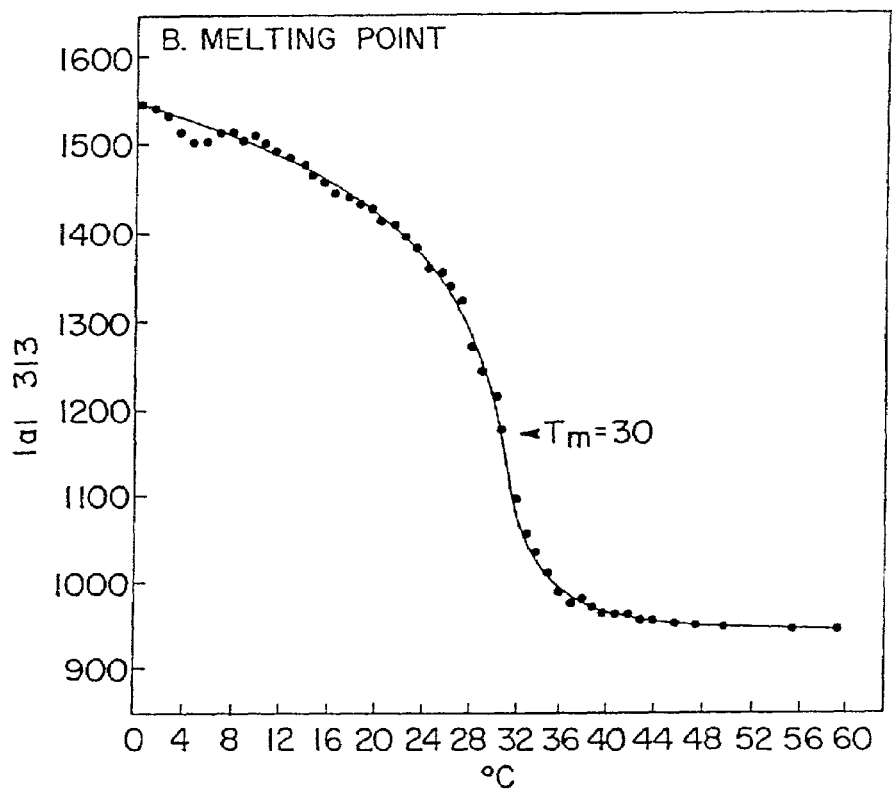
FIG. 4 records the change in optical rotation caused by a solution of the peptide of FIG. 3, as a function of increasing temperature, indicating its restricted conformation at the lower temperature.

The cell attachment promoting Ary-Gly-Asp sequence of the linear peptide generated as in Example I was conformationally restrained by allowing the peptide to assume a helical structure, according to methods of Dedhar et al, (1987) J. Cell Biol. 104:585, which is incorporated hereby reference. Briefly, a 33-amino acid peptide having the sequence (Pro-Hyp-Gly)$_4$-Ala-Pro-Gly-Leu-Arg-Gly-Asp-Thr-Gly-(Pro-Hyp-Gly)$_4$ was synthesized using an automated peptide synthesizer (Model 430A; Applied Biosystems, Foster City, Calif.). The sequence was confirmed by automated Edman degradation using a gas phase sequencer (Moder 470A; Applied Biosystems, Foster City, Calif.) as shown in FIG. 3. The linear peptide was allowed to dissolve overnight in the smallest possible volume of 0.05% acetic acid at 4° C. Polarimetrical analysis was used to confirm that it had assumed a helical structure according to the method of Rhodes et al., (1978) Biochemistry, 17:3442, which is incorporated herein by reference. The peptide existed as a triple helix at low temperatures as judged by the high degree of negative optical rotation which underwent a sharp change as the temperature was increased, producing a "melting" curve having an inflection point (second derivative equal to 0; Tm) at 30° C., as shown in FIG. 4.

EXAMPLE IV

Formation of an Alpha Helical Structure

An Arg-Gly-Asp containing peptide was designed so as to have an amino acid sequence such that it would under appropriate conditions assume an alpha helical configuration. As demonstrated by Carbone et al., (1987) J. Immunology 138:1838, which is incorporated herein by reference, peptides comprising alternating α-aminoisobutyric acid (α-ABA) and alanine (Ala) residues adopt helical conformations in structure-forming organic solvents. Moreover, the presence of a negatively charged group at the amino terminus and a positively charged group at the carboxy terminus creates a dipole which acts to stabilize such a helix (Shoemaker et al., (1987), Nature 326:563, which is incorporated herein by reference). Further, the sequence of amino acids were chosen so as to create an amphiphilic secondary structure in which hydrophilic residues lie on one side, lipophilic residues on the other side of the helix (Kaiser et al., (1984) Science, 223:249, which is incorporated herein by reference).

The following linear sequence was produced by an automated peptide sequencer (Model 430A; Applied Biosystems, Foster City, Calif.) was: SuccAla-Leu-Glu-Glu-αABA-Ala-Lys-Arg-Gly-Asp-Ser-Leu-αABA-Gly-Lys-αABA-Ala-Lys.

Figure 5:
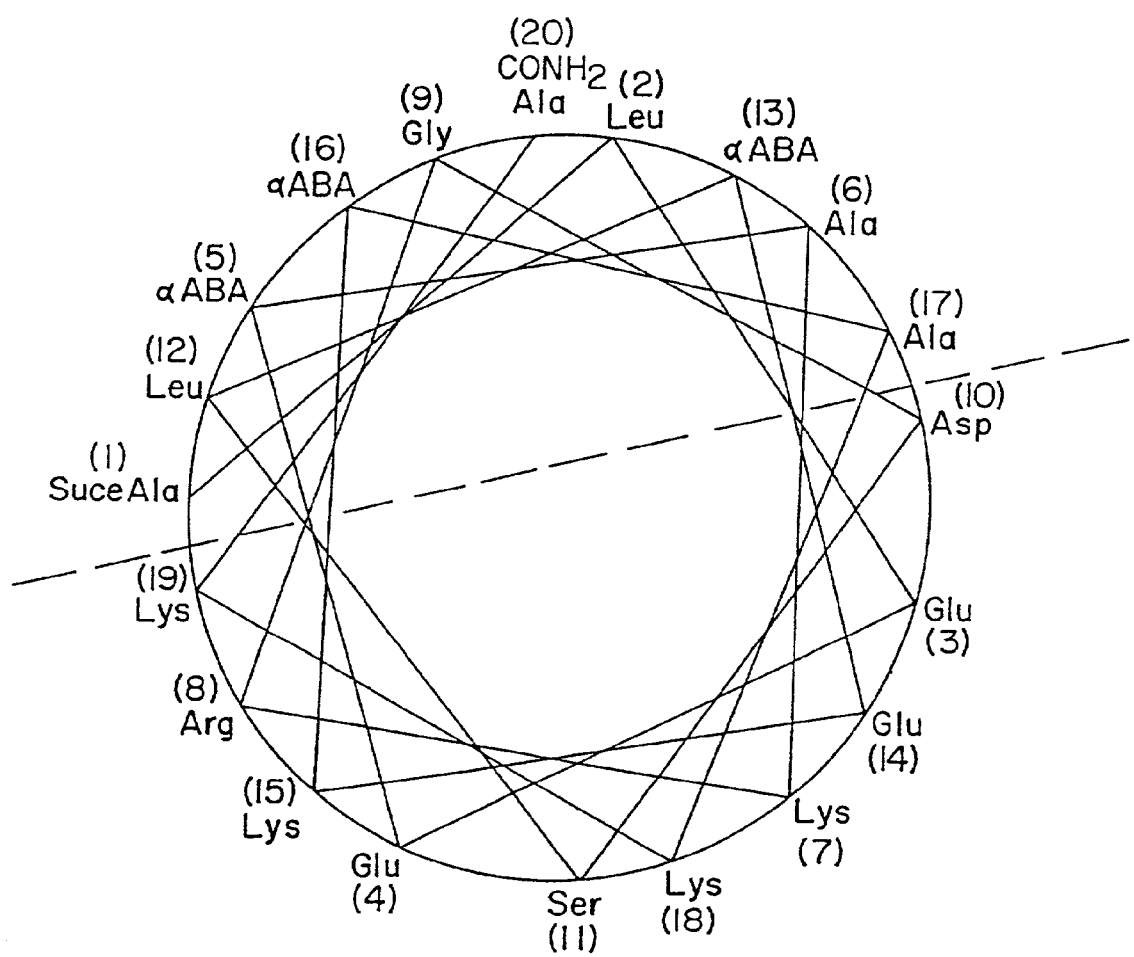
FIG. 5 is an axial projection of the peptide of Example IV. Those residues above the dotted line are lipophilic while those below the line are hydrophilic.

The peptide was synthesized and purified according to the methods of Example 1. The alpha helical conformation of this peptide is depicted schematically in FIG. 5.

EXAMPLE V

Cell Adhesion Assay

Fibronectin and vitronectin were purified from human plasma according to the methods of Ruoslahti et al., (1982) Meth. Enz. 82:803; and Hayman et al., (1983) PNAS 80:4003, respectively, both of which are incorporated herein by reference. The adhesion of normal rat kidney cells to fibronectin and vitronectin was assayed as described, in Ruoslahti et al., Meth. Enz. supra. Briefly, 0.1 ml solution of fibronectin or vitronectin at a concentration of 12 μg/ml in 0.1M PBS was placed in each well of 96-well plastic microtiter plates and left for 2 hours at room temperature. The unattached protein was removed by washing three times with PBS.

One day before the assay, a confluent culture of normal rat kidney cells was split 1:2 using standard tissue culture trypsin. The cells were washed three times with PBS, pH 7.2. 10 ml of 2× crystallized trypsin (Sigma, Type III), 0.1 mg/ml in PBS, was added, and the cells incubated at 37° C. until they detached. The detached cells were then collected by centrifugation and washed three times with a solution of 0.5 mg/ml of soybean trypsin inhibitor in PBS to ensure neutralization of the trypsin. Before the last centrifugation, a sample was taken and cell numbers and viability by trypan blue exclusion are determined. The cells were suspended in minimal essential medium (MEM) at a concentration of $10^6$ cells/ml and dispersed by pipetting until a single-cell suspension was obtained.

To ensure even dispersal of the cells in the microtiter well, 0.1 ml of MEM was added to each well, followed by the addition of 0.1 ml of the cell suspension. The plate was incubated for 1 hour at 37° C.

The unattached cells were removed simply by removing the medium and washing the wells. The plate was flooded with PBS, and the washing solution was removed. The cells were then fixed with 3% paraformaldehyde in PBS and stained with 1% toluidine blue, paraformaldehyde in PBS, and attached cells counted. Their number was determined using a cell counter that is capable of counting cells attached to a surface (Dynatech Laboratories, Alexandria, Va.).

The ability of the cyclized peptide of the invention to inhibit adhesion of cells to the substrates was assayed by adding stock solutions of the peptide dissolved in MEM to give final concentrations in the wells of 0 to 10.0 mM. Prior to addition to the assay, the stock solutions were neutralized with sodium bicarbonate. Rat kidney cells were added and the wells incubated and assayed as described.

Figure 2:
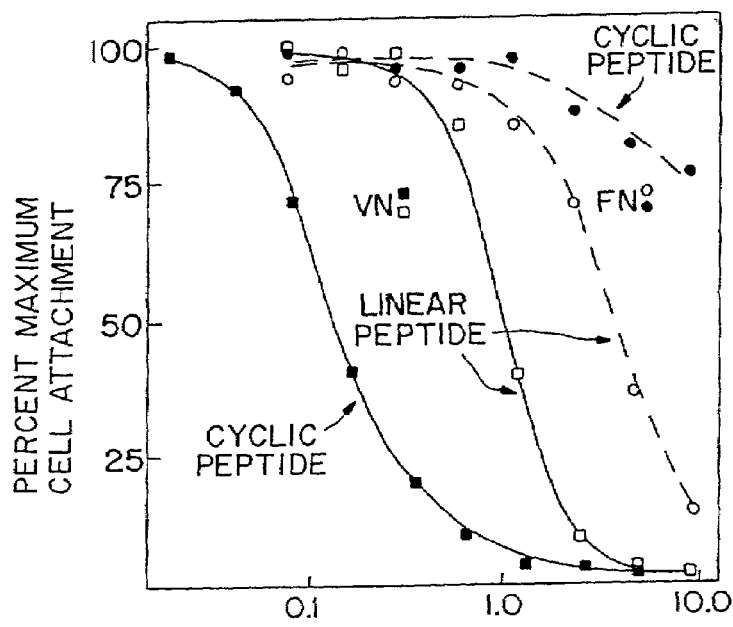
FIG. 2 is a graph illustrating adhesion of normal rat kidney cells to fibronectin and vitronectin in the presence of a cyclic and a linear peptide having the same amino acid sequence.

In order to more fully determine the ability of the cyclized peptide to inhibit the attachment of normal rat kidney cells to the fibronectin and vitronectin substrates, the binding of a non-cyclized, or linear, peptide having the sequence Gly-Pen-Gly-Arg-Gly-Asp-Ser-Pro-Cys was assayed. As shown in FIG. 2, the cyclic peptide of the invention inhibited attachment to vitronectin at a 10-fold lower molar concentration than the linear peptide, but it was ineffective at inhibiting attachment to fibronectin. The linear peptide, in contrast, inhibited attachment of cells to both substrates at relatively similar concentrations.

While not wishing to be bound by this explanation, the cyclic peptide of the invention appears to possess a different affinity for the binding site of fibronectin and vitronectin receptors. This is consistent with the fact that the rat kidney cells used in the assay are known to possess separate receptors for fibronectin and vitronectin.

EXAMPLE VI

Cyclization Through Peptide Bond

The peptide cyclo-(1-7)Gly-Arg-Gly-Asp-Ser-Pro-Asp-Gly was synthesized using a modification of the method of Schiller et al., Int. J. Peptide Protein Res. 25:171 (1985), which is incorporated herein by reference.

Figure 6:
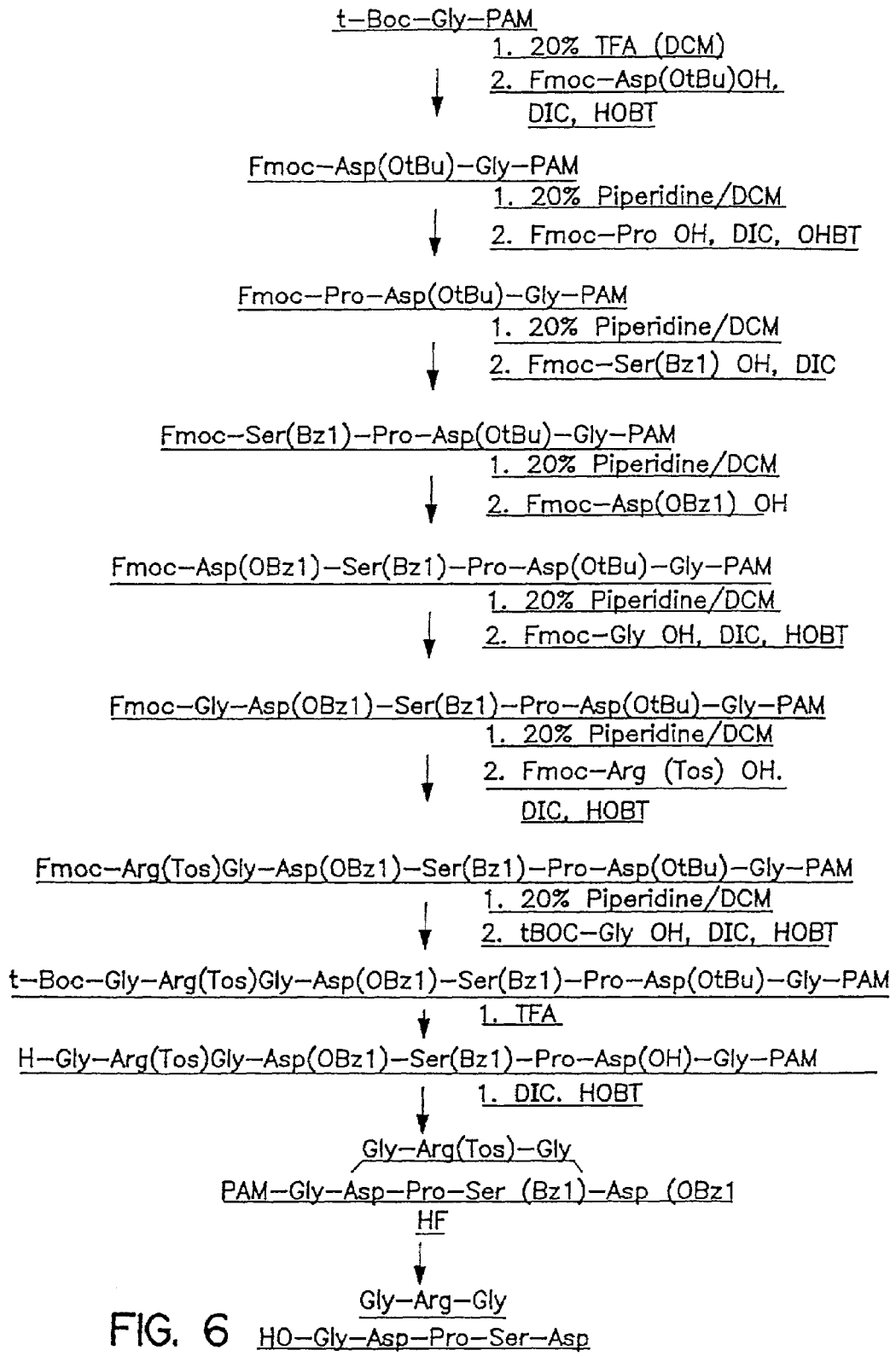
FIG. 6 is a schematic representation of the cyclic peptide synthesized in Example VI.

The synthesis was done using PAM resin-TFA: (Applied Biosystems, Inc., Foster City, Calif.) with t-Boc Gly-attached to the resin withd a substitution factor of 0.80 mmol/g (see FIG. 6). All amino acids were obtained from Bachem Bioscience, Inc., Philadelphia, Pa. 1.25 g (1.0 mmol) of resin was shaken with 20 ml dichloromethane (DCM) for 15 minutes to induce swelling and DCH removed with $N_2$ pressure the procedure repeated. The t-Boc protecting group was cleaved with 20 ml 20% TFA; (Applied Biosystems, Inc., Foster City, Calif.) in DCH (Pfizer, Groton, Conn.) for 15 minutes. This reaction was repeated, this time shaking for 30 minutes. Between the reactions, the resin was washed once with 20 ml DCH for 2 minutes. After the second reaction, the resin was washed six times with 20 ml DCM for 2 minutes each, followed by neutralization with 20 ml 10% triethylamine (TEA) in DCH two times for 3 minutes each. The resin was washed six times with 20 ml DCM for 2 minutes each and was then ready for the next reaction.

In a 50 ml round bottom flask equipped with stirring bar, Fmoc-Asp-t-butyl ester ((OtBu)OH) (1.03 g, 2.5 mol) was dissolved in 15 ml DCM followed by addition of 2.5 ml (1M) DIC (Aldrich Chem. Co., Milwaukee, Wis.) in DCM. The mixture diisopropyl carbodiimide was stirred for 5 minutes and followed by addition of 1.25 ml 2.0 M hydroxybenzotriazole (HOBT; Aldrich) in DMF (Pfizer) at 0° C. and stirred for 10–15 minutes more. This mixture was added to the resin and shaken 1 to 2 hours. This reaction was repeated once (double coupled) and the resin was washed 2 times with 20 ml DCM between couplings. After the second coupling was completed, the resin was washed three times with 20 ml DCM.

The cleavage of the Fmoc group was done With 20 ml 20% piperidine (Aldrich) in DCM (freshly made) and shaken for 15 minutes. This reaction was repeated for another 30 minutes. The resin was then washed once with DMF and five times with DCM for 2.0 minutes each. Then the resin was ready for the next coupling.

In a 50 ml round bottom flask equipped with stirring bar, Fmoc-Pro-OH (0.84 g, 2.5 mmol) was dissolved in 15 ml DCH followed by addition of 2.5 ml (1 M) DIC in DCM. The mixture was stirred for 5.0 minutes, followed by the addition of 1.25 ml (2M) HOBT in DMF at 0° C. and stirred for 10 to 15 minutes more. This mixture was added to the resin and shaken 1 to 2 hours. This reaction was repeated once (double coupled) and the resin was washed 2 times with 20 ml DCM between couplings. After the second coupling was completed, the resin was washed three times with 20 ml DCM. The Fmoc was cleaved using the same procedure as above and the material was then ready for the next coupling.

In a 50 ml round bottom flask equipped with stirring bar, Fmoc-Asp-benzyl ester ((OBzl)-OH) (1.11 g, 2.5 mol) was dissolved in 15 ml DCM followed by addition of 2.5 ml (1 M) DIC in DCM. The mixture was stirred for 5.0 minutes, followed by addition of 1.25 ml 2.0 M HOBT in DMF at 0° C. and stirred for 10 to 15 minutes more. This mixture was added to the resin and shaken 1 to 2 hours. This reaction was repeated once (double coupled) and the resin was washed 2 times with 20 ml DCM between couplings. After the second coupling was completed the resin was washed three times with 20 ml DCM. The Fmoc was cleaved using the same procedure as above and the material was then ready for the next coupling.

In a 50 ml round bottom flask equipped with stirring bar, Fmoc-Gly-OH (0.74 g, 2.5 mmol) was dissolved in 15 ml DMF followed by addition of 2.5 ml (1 M) DIC in DCM. The mixture was stirred for 5.0 minutes, followed by addition of 1.25 ml 2.0 M HOBT in DMF at 0° C. and stirred for 10 to 15 minutes more. This mixture was added to the resin and shaken 1 to 2 hours. This reaction was done twice (double coupled) and the resin was washed 2 times with 20 ml DCM in between coupling. After the second coupling was completed the resin was washed three times with 20 ml DCM. The Fmoc was cleaved using the same procedure as above and the material was then ready for the next coupling.

In a 50 ml round bottom flask equipped with stirring bar, Fmoc-Arg Tosilate ((Tos)OH) (1.37 g, 2.5 mmol) was dissolved in 15 ml DCH followed by addition of 2.5 ml (1M) DIC in DCM. The mixture was stirred for 5.0 minutes and followed by addition of 1.25 ml 2.0 M HOBT in DMF at 0° C. and stirred for 10 to 15 minutes more. This mixture was added in to the resin and shaken 1 to 2 hours. This reaction was repeated once (double coupled) and the resin was washed 2 times with 20 ml DCM in between coupling. After the second coupling was done the resin was washed three times with 20 ml DCM. The Fmoc deprotection was performed using the same as the procedure above and the material was then ready for the next coupling.

In a 50 ml round bottom flask equipped with stirring bar, t-Boc-Gly-OH (0.44 g, 2.5 mmol) was dissolved in 15 ml DCM followed by addition of 2.5 ml (1M) DIC in DCM. The mixture was stirred for 5.0 minutes and followed by addition of 1.25 ml (2M) HOBT in DMF at 0° C. and stirred for 10 to 15 minutes more. This mixture was added in to the resin and shaken 1 to 2 hours. This reaction was repeated (double coupled) and the resin was washed 2 times with 20 ml DCM in between coupling for 2 minutes each. After the second coupling was done the resin was washed three times with 20 ml DCH for 2 minutes each.

The deprotection of the t-Boc Group of Gly 1 and the t-Butyl ester side chain of Asp 7 was performed at the same time by adding 20 ml 20% TFA in DCM for 15 minutes. This reaction was repeated once again for 30 minutes. Between reactions the resin was washed once with DCM for 2 minutes. After the second reaction, the resin was washed six times with 20 ml DCM for 2 minutes each, followed by neutralization with 20 ml 10% TEA in DCM two times for 3 minutes each. The resin was washed six times with 20 ml DCM for 2.0 minutes each.

The N-terminus of Gly 1 was cyclized to the side chain carboxyl group of Asp 7. The cyclization was accomplished, by adding 10 ml of 1M DIC solution and 5 ml 2M HOBT in DMF and shaken for 4 days. Each day, old reagent was drained and the resin was washed with 20 ml DMF once and with DCM three times for 2 minutes each. Fresh reagent (DIC and HOBT) was then added.

The resin was cleaved with hydrogen fluoride using procedures well known in the art. After cleaving, the peptide-containing resin was were washed with cold ethyl ether then dissolved with 10% acetic acid to remove the peptide from the resin. The filtrate was frozen and lyophilized. The crude product recovered was 508 mg. This crude product was subjected to purification using HPLC through $C_{18}$ (1×20 cm; 10-µm packing) column. The peptide was loaded on the column in buffer A (10 mM ammonium acetate at pH 6.0)

and eluted with a gradient of buffer B consisting of 60% acetonitrile and 40% buffer A. Yield after purification was 210 mg.

This compound was confirmed to have the desired cyclic peptide structure by proton NMR in DMSO-d6 as the solvent. The 1D and 2D (COSY, COSY-Relay, and NOESY) spectra of this compound were obtained by using a 360 MHz FT-NMR equipped with Nicolet software at the University of California, San Diego NMR facility. (See Wuthrich, K., NMR of Proteins and Nucleic Acids, John Wiley & Son, NY (1986), which is incorporated herein by reference).

Although the invention has been described with reference to the presently-preferred embodiment, it should be understood that various modifications can be made by those skilled in the art without departing from the invention. Accordingly, the invention is limited only by the following claims.

We claim:

1. A method of inhibiting binding of a natural ligand to a vitronectin receptor comprising contacting said vitronectin receptor with a cyclic peptide containing the sequence Arg-Gly-Asp, said Arg-Gly-Asp sequence being conformationally restricted, thereby selectively inhibiting binding of said natural ligand to said vitronectin receptor with respect to the function of other receptors.

2. The method of claim 1, wherein said inhibition occurs in vivo.

3. A method of selectively inhibiting attachment of cells to vitronectin comprising providing to said cells in vitro a solution of a cyclic peptide containing the sequence Arg-Gly-Asp, said Arg-Gly-Asp sequence being conformationally restricted, thereby selectively inhibiting attachment of said cells to said vitronectin.

4. A method of selectively inhibiting attachment of cells to vitronectin comprising providing to said cells in vivo a solution of a peptide containing the sequence Arg-Gly-Asp, said Arg-Gly-Asp sequence being conformationally restricted, thereby selectively inhibiting attachment of said cells to said vitronectin.

5. A method of selectively inhibiting binding of vitronectin receptor-containing cells to a substrate comprising providing to said cells in vitro a solution containing a cyclic peptide that encompasses the sequence Arg-Gly-Asp, said Arg-Gly-Asp sequence being conformationally restricted, thereby selectively inhibiting binding of said vitronectin receptor-containing cells to said substrate.

6. A method of selectively inhibiting binding of vitronectin receptor-containing cells to a substrate comprising providing to said cells in vivo a solution containing a peptide that encompasses the sequence Arg-Gly-Asp, said Arg-Gly-Asp sequence being conformationally restricted, thereby selectively inhibiting binding of said vitronectin receptor-containing cells to said substrate.

7. A method of selectively inhibiting binding of vitronectin receptor-containing cells to a substrate comprising the steps of:
   a. providing to said cells in vitro a cyclic peptide containing the sequence Arg-Gly-Asp in solution, said Arg-Gly-Asp sequence being conformationally restricted; and
   b. contacting said cells with said solution.

8. A method of selectively inhibiting binding of vitronectin receptor-containing cells to a substrate comprising the steps of:
   a. providing to said cells in vivo a peptide containing the sequence Arg-Gly-Asp in solution, said Arg-Gly-Asp sequence being conformationally restricted; and
   b. contacting said cells with said solution.

9. A method of selectively inhibiting binding of cells to a substrate comprising providing to said cells in vitro a solution of a peptide containing an Arg-Gly-Asp sequence chemically modified with an additional chemical structure, wherein said additional chemical structure conformationally restricts the stereochemical structure of said Arg-Gly-Asp sequence in such a way that the affinity of the Arg-Gly-Asp binding site sequence for a particular receptor is enhanced.

10. A method of selectively inhibiting binding of cells to a substrate comprising providing to said cells in vivo a solution of a peptide containing an Arg-Gly-Asp sequence chemically modified with an additional chemical structure, wherein said additional chemical structure conformationally restricts the stereochemical structure of said Arg-Gly-Asp sequence in such a way that the affinity of the Arg-Gly-Asp binding site sequence for a particular receptor is enhanced.

11. The method of claim 4, wherein said peptide is a cyclic peptide.

12. The method of claim 6, wherein said peptide is a cyclic peptide.

13. The method of claim 8, wherein said peptide is a cyclic peptide.

* * * * *